(12) United States Patent
Christoff et al.

(10) Patent No.: US 9,259,295 B2
(45) Date of Patent: Feb. 16, 2016

(54) METHODS AND APPARATUS FOR MAKING A POLYMERIC ORTHODONTIC APPLIANCE

(75) Inventors: James D. Christoff, Birchwood, MN (US); Richard E. Raby, Lino Lakes, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 721 days.

(21) Appl. No.: 13/225,591

(22) Filed: Sep. 6, 2011

(65) Prior Publication Data

US 2012/0061868 A1 Mar. 15, 2012

Related U.S. Application Data

(60) Provisional application No. 61/381,289, filed on Sep. 9, 2010.

(51) Int. Cl.
*A61C 7/02* (2006.01)
*A61C 7/08* (2006.01)
*A61C 7/00* (2006.01)

(52) U.S. Cl.
CPC .... *A61C 7/08* (2013.01); *A61C 7/00* (2013.01)

(58) Field of Classification Search
CPC .................................. A61C 7/00; A61C 7/02
See application file for complete search history.

(56) References Cited

U.S. PATENT DOCUMENTS

| | | | |
|---|---|---|---|
| 5,011,406 A | 4/1991 | Wildman | |
| 5,028,232 A * | 7/1991 | Snow | 433/24 |
| 5,915,968 A * | 6/1999 | Kirsch et al. | 433/173 |
| 6,210,162 B1 | 4/2001 | Chishti | |
| 6,227,851 B1 | 5/2001 | Chishti | |
| 6,394,801 B2 | 5/2002 | Chishti | |
| 6,499,997 B2 | 12/2002 | Chishti | |
| 6,629,840 B2 | 10/2003 | Chishti | |
| 7,108,508 B2 | 9/2006 | Hedge | |
| 7,578,674 B2 | 8/2009 | Chishti | |
| 2004/0191728 A1* | 9/2004 | Miller | 433/213 |
| 2004/0265769 A1* | 12/2004 | Inman | 433/21 |
| 2006/0121408 A1 | 6/2006 | Hedge | |
| 2006/0191772 A1* | 8/2006 | Wiggins et al. | 198/499 |
| 2006/0257814 A1* | 11/2006 | Chishti et al. | 433/24 |
| 2007/0243502 A1* | 10/2007 | Wen | A61C 7/00 433/214 |
| 2008/0026338 A1 | 1/2008 | Cinader | |
| 2008/0233531 A1 | 9/2008 | Raby | |

FOREIGN PATENT DOCUMENTS

| | | |
|---|---|---|
| CN | 101273921 | 10/2008 |
| EP | 1369091 | 12/2003 |

* cited by examiner

*Primary Examiner* — Ryan Ochylski
(74) *Attorney, Agent, or Firm* — Kevin W. Weber

(57) ABSTRACT

A series of polymeric orthodontic appliances is made by providing a set of tooth analogs, each having a model crown that represents the shape of a corresponding tooth of the patient. The tooth analogs are moved along respective guides as needed in order to bring the associated model crown an incremental step toward or away from its desired position. The polymeric appliance is formed by placing a sheet of polymeric material over the model crowns after at least one tooth analog has been moved to create a desired model tooth arrangement.

21 Claims, 5 Drawing Sheets

METHODS AND APPARATUS FOR MAKING A POLYMERIC ORTHODONTIC APPLIANCE

RELATED APPLICATION DATA

This application claims the benefit of U.S. Provisional Application Ser. No. 61/381,289, filed Sep. 9, 2010, the disclosure of which is incorporated by reference herein.

BACKGROUND OF THE INVENTION

1. Field of the Invention

This invention relates to methods and apparatus for making an orthodontic appliance that is comprised of a clear polymeric material.

2. Description of the Related Art

Orthodontic treatment involves movement of misaligned or crooked teeth to improved positions. Orthodontic treatment can greatly enhance the patient's facial appearance, especially in areas near the front of the patient's oral cavity. In certain instances, orthodontic treatment can also improve the occlusion in such a manner that opposing teeth will function better with each other during mastication.

One type of common orthodontic treatment includes the use of a set of brackets, each of which is affixed to a respective tooth in the patient's mouth. A resilient arch-shaped wire is placed into a slot of each bracket and functions as a track to guide movement of the bracket and hence the associated tooth to desired positions. Ends of the wire are often retained in channels of small devices known as buccal tubes that are secured to the patient's molar teeth.

Another type of orthodontic treatment involves the use of resilient polymeric trays that fit over the teeth of the patient's dental arches. These trays, also known as aligners, alignment shells and polymeric appliances, are provided in a series and are intended to be worn in succession in order to gradually move the teeth in incremental steps toward a desired target arrangement. Some types of polymeric appliances have a row of tooth-shaped cavities for receiving each tooth of the patient's dental arch, and the cavities are oriented in slightly different positions from one appliance to the next in order to incrementally urge each tooth toward its desired target position by virtue of the resilient properties of the polymeric material.

A variety of methods have been proposed in the past for manufacturing polymeric appliances. According to one known method, a digital data file is obtained that represents the patient's upper and lower dental arches at the beginning of treatment. This data file is then analyzed to identify subsets of data, each of which represents one of the patient's teeth. Next, a technician then uses a computer input device (such as a mouse or keyboard) to virtually reposition the maloccluded teeth and move individual teeth on a computer screen relative to each other into desired target positions. The target positions are then reviewed and approved by a treating professional, such as an orthodontist that is located remotely from the technician.

Once the proposed tooth arrangement has been approved, the data representing the initial tooth positions and the data representing the target tooth positions are then used to determine intended intermediate positions of the teeth as the teeth move from initial to target positions. As one example, data representing the differences in tooth positions between the initial tooth arrangement and the target tooth arrangement may be interpolated in order to obtain a series of twenty intermediate positions of the teeth. The data representing those intermediate tooth positions is then stored in memory and subsequently used to make models of the dental arches for each intermediate tooth arrangement.

For example, a data set representing the teeth in a desired target arrangement and twenty data sets representing the teeth in twenty different intermediate arrangements may be used to manufacture a series of twenty-one physical, positive dental arch models for each dental arch using rapid prototyping methods such as stereolithography. Subsequently, a sheet of polymeric material is placed over each of the arch models and formed under heat, pressure and/or vacuum to conform to the model teeth of each model arch. The formed sheet is cleaned and trimmed as needed and the resulting arch-shaped appliance is shipped along with the remaining appliances to the treating professional. The patient is then instructed to wear each appliance over its intended dental arch in sequence for a period of, for example, two or four weeks, after which the used appliances are discarded and the next two appliances in the series for the upper and lower dental arches are to be worn.

SUMMARY OF THE INVENTION

Certain shortcomings are encountered when carrying out the methods described above for making polymeric appliances. For example, the process of manufacturing a physical dental arch model corresponding to each polymeric appliance is somewhat time-consuming and expensive, especially if the cost of the rapid prototyping material is relatively high. If, for instance, a series of twenty polymeric appliances is requested for both the upper and lower dental arches, a total of forty physical models must be manufactured. Storage and disposal of the physical models also represent manufacturing expenses that may be significant.

The present invention is directed toward improved methods and apparatus for making a polymeric orthodontic appliance, and involves providing a set of physical tooth analogs along with a guide corresponding to at least some of the tooth analogs. The tooth analogs include model crowns that represent the patient's teeth. The guides are constructed to direct movement of the tooth analogs along a path that enables the corresponding model tooth crowns to shift along a path between initial positions and target positions.

The tooth analogs are moved in incremental steps as desired and a polymeric appliance is formed over the model tooth crowns after the desired incremental steps have been achieved. In one embodiment, one or more tooth analogs are moved an incremental step from an initial position in a direction toward a desired target position so that the model crowns are moved to a first tooth arrangement that represents a first target stage of treatment. A polymeric appliance is then formed over the model crowns and designated as the first appliance in the series to be worn by the patient. The method is then repeated as many times as desired in order to manufacture a complete series of polymeric appliances for ultimately moving the patient's teeth from an initial to a desired target arrangement.

In more detail, a method of making a polymeric orthodontic appliance according to one embodiment of the invention comprises:

providing a set of physical tooth analogs each having a model tooth crown with a shape that is representative of the shape of a respective tooth crown in a patient's dental arch;

obtaining data for at least some of the tooth analogs that represents a path of movement for the corresponding model crown to a desired position;

using the data to construct a set of guides for guiding the movement of the tooth analogs in such a manner that the respective model crowns are moved along corresponding paths;

moving one or more of the tooth analogs along their respective guides as needed in order to bring the corresponding model crown an incremental step either toward or away from its desired position; and forming the polymeric appliance over the model crowns after at least one of the tooth analogs has been moved.

Another embodiment of the invention is directed toward apparatus for making a polymeric appliance. The apparatus comprises a set of model teeth including at least one tooth analog having a model tooth crown with a shape that is representative of the shape of a respective tooth crown in a patient's dental arch. The apparatus additionally includes a guide for the tooth analog, wherein the guide includes a track in contact with the tooth analog for guiding movement of the model tooth crown along a predetermined path of travel.

Advantageously, the present invention can be carried out using only a single model of each of the patient's dental arches, since individual model tooth crowns in the model arches can be manipulated as desired for forming each of the polymeric appliances. Moreover, by manually manipulating the tooth analogs and observing movement of the model tooth crowns, the technician may be able to observe that a certain sequence of movements may be preferable to another sequence. For instance, the technician may observe that less interference with neighboring teeth might occur if the long axis of the tooth is urged toward a more upright position before a desired rotation of the tooth about its long axis is achieved. Such observations using a physical tooth model may be preferred by some technicians over attempts to observe movements of virtual teeth on a two-dimensional computer display.

These and other aspects of the invention will be described in the paragraphs that follow and are illustrated in the accompanying drawings.

DEFINITIONS

As used herein:

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF THE PREFERRED EMBODIMENTS

Figure 1:
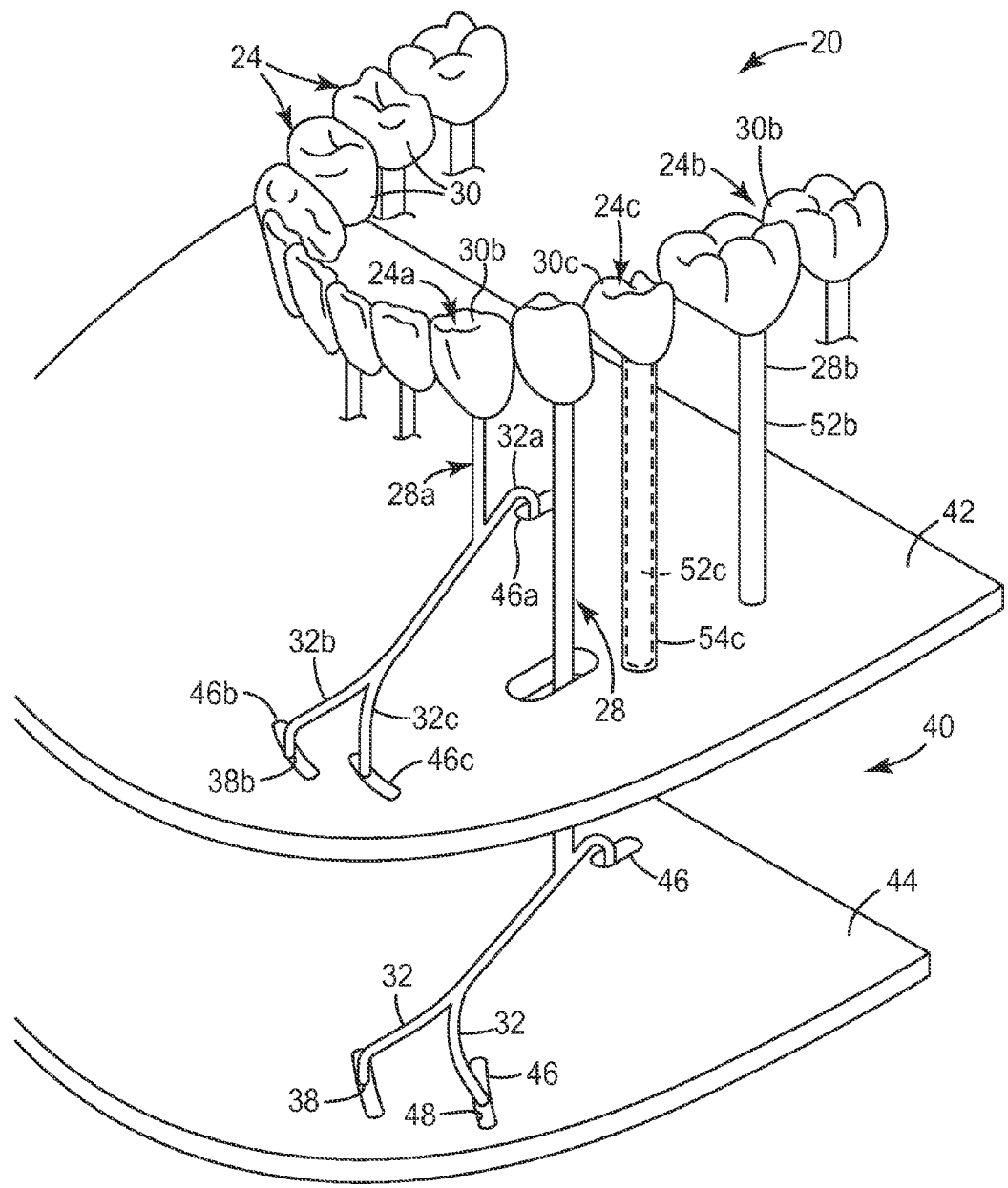
FIG. 1 is a perspective view with parts broken away in section of a portion of an apparatus for making a polymeric appliance in accordance with one embodiment of the invention.
Figure 6:
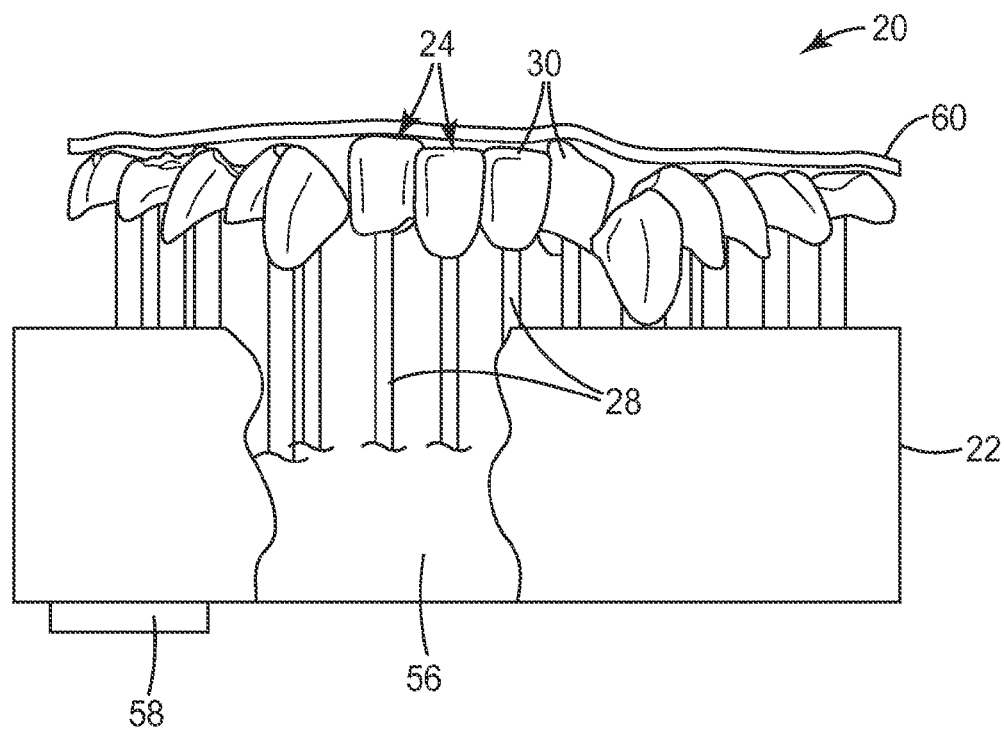
FIG. 6 is a side elevational view of another portion of the apparatus shown in FIG. 1 with parts broken away in section, and additionally showing a sheet of polymeric material that is being formed over tooth analogs of the apparatus.

An apparatus 20 for making a polymeric appliance according to one embodiment of the present invention is depicted in FIGS. 1 and 6 and includes an open-top container or pan 22 (shown only in FIG. 6). The apparatus also includes a set of individually movable tooth analogs 24. Preferably, the set of tooth analogs 24 includes a sufficient number of tooth analogs 24 to represent each tooth of one of a patient's dental arches. Each of the tooth analogs 24 includes a base 28 and a model crown 30 that is fixedly connected to the base 28. Optionally, a second, similar apparatus can be constructed for making polymeric appliances for the patient's remaining dental arch.

Preferably, each model crown 30 has a configuration that is identical or at least closely similar in configuration to the configuration of the crown of the patient's corresponding tooth. Each model crown 30 includes outer surfaces that represent the exposed enamel surfaces of the patient's crown that lie above the patient's gingiva. Some of the bases 28 include one or more legs 32 that extend in a direction away from the model crown, and each leg 32 has an outer end 38 that is remote from the model crown 30.

As one example, the set of tooth analogs 24 includes a tooth analog 24a corresponding to the orthodontic patient's lower left lateral incisor tooth. The tooth analog 24a is shown in more detail in FIGS. 2-4 and includes a base 28a and a model lower left lateral incisor tooth crown 30a that is connected to the base 28a. In the exemplary embodiment illustrated in FIGS. 1-4, the base 28a includes three legs 32a, 32b, 32c with outer ends 38a, 38b, 38c respectively. The outer ends 38a, 38b, 38c are spaced apart from each other as well as the outer ends 38 of each remaining tooth analog 24.

A platform 40 (shown in FIGS. 1, 2 and 4) extends across the bottom of the pan 22. As one option, the platform 40 is manufactured as a distinct, initially separate component that is subsequently placed in the bottom of the pan 22 during assembly of the apparatus 20. Alternatively, the platform 40 may be integral with the bottom of the pan 22 and manufactured together with the upright walls of the pan 22 in a single manufacturing operation. The platform 40 is constructed with a number of guides or tracks 46 and preferably includes three tracks 46 for at least one of the tooth analogs 24 that has been designated for movement. Each of the tracks 46 includes a channel 48 with a longitudinal axis.

For example, the platform 40 includes three tracks 46a, 46b, 46c that are associated with the legs 32a, 32b, 32c respectively of the tooth analog 24a. Optionally, the outer ends 38a, 38b, 38c each comprise an enlarged head that is captured in its respective track 46a, 46b, 46c by means of physically interlocking configurations. In the illustrated embodiment, the top of each track 46 includes two wall portions that overhang the channel 48 and are spaced apart from each other to present an elongated slot. The width of the slot is narrower than the width of the associated outer end 38 in order to capture the corresponding outer end 38 in the channel 48 while enabling movement of the associated leg 32 along the longitudinal axis of the channel 48.

The legs 32 may have any one of a number of different configurations and extend in any one of a number of different directions in accordance with the particular, desired path of travel of the associated model crown 30. In the illustrated example of the tooth analog 24a, the leg 32a extends away from the model crown 30a in a downward direction as well as in a horizontal lingual direction, while both of the legs 32b, 32c extend away from the model crown 30a in a downward direction as well as in a horizontal facial direction.

The tracks 46 are constructed to guide and enable movement of the legs 32 in respective directions that will permit movement of the model crown 30 in directions along a predetermined, intended path of travel. To this end, the longitudinal axes of the channels 48 are arranged in directions as may be needed to guide movement of the associated model crown 30 along its intended path of travel. The channels 48 of the tracks 46 may extend along curved or straight paths and/or extend along inclined paths that rise or fall in a vertical direction, and need not extend along parallel paths. Each channel 48 has a first closed end and a second closed end that is remote from its first end.

Figure 2:
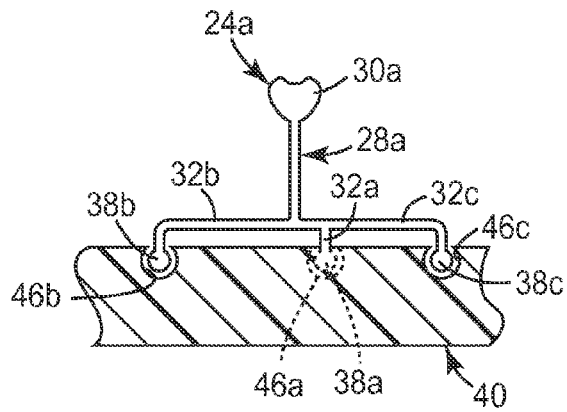
FIG. 2 is an enlarged end view of a portion of the apparatus illustrated in FIG. 1, and showing one of the tooth analogs that is movable along guide tracks of the apparatus.
Figure 3:
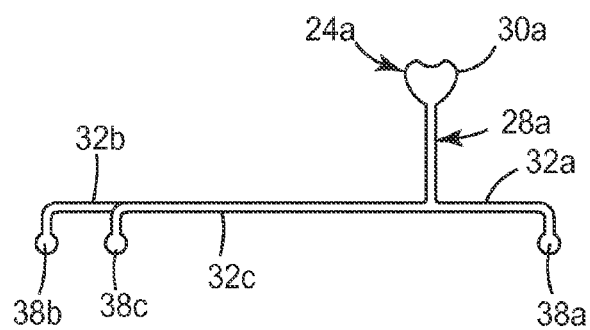
FIG. 3 is an enlarged side view of the tooth analog alone that is shown in FIG. 2.
Figure 4:
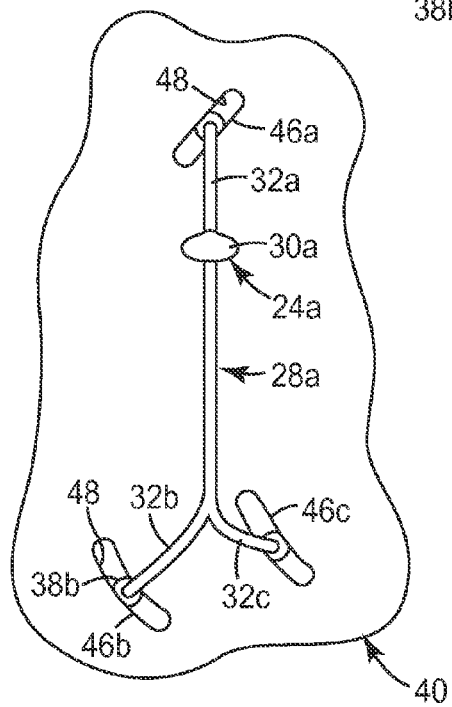
FIG. 4 is an enlarged top view of the tooth analog and the guide tracks illustrated in FIG. 2.

In the exemplary embodiment depicted in FIGS. 2-4, the track 46a extends in a generally straight lingual direction as its second channel end is approached. The tracks 46b, 46c are slightly longer in length than the track 46a and rise along upwardly inclined curved arcs that extend about a vertical reference axis as the corresponding second channel ends are approached As a result, the longitudinal axis of the model crown 30a is moved toward an upright orientation and the model crown 30a is simultaneously pivoted about its longitudinal axis as the legs 32a, 32b, 32c are moved along the corresponding tracks 46a, 46b, 46c from the first channel ends and to the second channel ends.

Alternatively, if only a relatively simple, horizontal translational movement of the model crown 30 is desired, the associated tracks 46 are constructed with straight longitudinal axes that extend parallel to each other in a horizontal reference plane. As another example, if only rotation of the model crown 30 about its longitudinal axis is intended, the tracks 46 may extend along circular paths in a horizontal reference plane having a center of radius aligned with the longitudinal axis of the model crown 30. As yet another alternative, if only vertical movement of the model crown 30 in a gingival direction is needed, each of the legs 32 may be constructed to extend primarily in horizontal directions as its outer end 38 is approached; in addition, the corresponding tracks 46 are then constructed to extend along parallel, vertically-aligned paths such that rotation or tilting movements of the model crown 30 are prohibited as the legs 32 move along the channels 48.

A multitude of other variations in the configuration of the tracks 46 as well as the legs 32 are also possible, including combinations of the foregoing examples. In this manner, any one of a variety of different motions of the model crown 30 can be achieved. Once the desired path of travel of the model crown 30 from its initial position representing the patient's tooth in its initial, maloccluded position to its target position representing the desired position of the patient's tooth at the conclusion of treatment is determined, the size, shape and orientation of the legs 32 and the associated tracks 46 can be determined and optimized to avoid interference with movement of adjacent model crowns 30 as well as to afford precise control over movement of the model crown 30.

Advantageously, the use of three legs for at least some tooth analogs 24 (such as tooth analog 24a as shown in the example of FIGS. 1-4) provides a tripod support arrangement that facilitates retaining the model crown 30 in a rigid, steady orientation during a subsequent manufacturing operations to form a set of polymeric appliances as will be further described in the paragraphs below. The enlarged outer ends 38 also serve to securely retain the legs 32 in coupled relation to the corresponding tracks 46 in order to avoid the possibility that one or more of the legs 32 may be raised free of the corresponding channel 48 and move the model crown 30 in an unintended manner as the tooth analog 24 is shifted from one position to another.

Additionally, the relatively long length of the legs 32a, 32b, 32c in the example shown in FIGS. 1-4 helps to facilitate precise, guided movements of the model crown 30a, since the outer ends 38a, 38b, 38c move over relatively large distances in comparison to the resulting movement of the model crown 30a. The relatively long length of the legs 32a, 32b, 32c also provides a lever arm that yields a mechanical advantage for the technician attempting to move the model crown 30a along its intended path of travel. Consequently, relatively small movements of the model crown 30a may be carried out with precision using only a relatively small, manual pushing force against the analog 24a.

The size and shapes of the legs 32 of each tooth analog 24, as well as the directions of extension of the legs 32 of each tooth analog 24, are selected to avoid interference with the legs 32 of the adjacent tooth analogs 24. To this end, and as shown in FIG. 1, the horizontal portion of the legs 32 of one tooth analog 24 may optionally extend in a horizontal reference plane that is vertically spaced from the horizontal portions of the legs 32 of the adjacent tooth analogs 24. Moreover, the platform 40 may include two or more levels that are spaced apart in vertical directions, such as level 42 and level 44 shown in FIG. 1. The levels may be connected together by a framework comprising webs of material used to make the platform 40.

As an alternative or in addition to the variations mentioned above, the horizontal portion of the legs 32 of one tooth analog 24 may all extend in a generally facial direction, while the horizontal portion of the legs 32 of the neighboring tooth analogs 24 may all extend in a generally lingual direction. In this embodiment, the interlocking construction between the outer ends 38 and the tracks 46 is arranged to enable the tracks 46 to support the tooth analog 24 in a cantilever fashion. Furthermore, if only rotation of the model crown 30 about its long axis is desired, one of the legs 32 can extend downward in general alignment with the long axis of the model crown 30 while the two remaining legs 32 can extend either in a lingual or a facial direction.

Optionally, the tracks 46 include structure that hinders free movement of the corresponding legs 32 in one direction, and/or facilitates moving the legs 32 a discrete, pre-defined amount in the opposite direction. In the example shown in FIG. 5, this structure comprises ratchet-like structure that includes a row of inclined ratchet teeth 50 arranged for contact with the leg 32 as the leg 32 moves along the track 46. The ratchet teeth 50 are deformable to enable movement of the leg 32 toward the second end of the channel 48 with relatively little resistance. However, the inclined, forward orientation of the ratchet teeth 50 provides substantially greater resistance to movement of the leg 32 if an attempt is made to move the leg 32 in a direction toward the first end of the channel 48.

Figure 5:
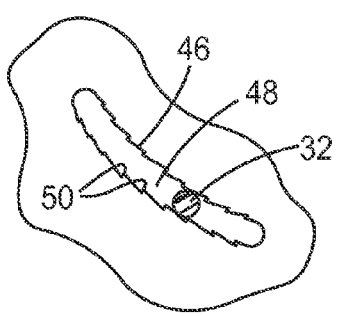
FIG. 5 is an enlarged top view of one of the guide tracks and a leg of the tooth analog shown in FIGS. 2-4, illustrating optional ratchet structure for hindering movement of the analog in a certain direction along the track.

In the embodiment shown in FIG. 5, the ratchet teeth 50 are provided along both sides of the slot that forms the top of the channel 48 and retains the outer end 38 in place. In another embodiment, the ratchet teeth 50 are provided along only one side of the slot that forms the top of the channel 48. In still another embodiment, the ratchet teeth 50 are located along the interior of the channel 48.

Optionally, the ratchet teeth 50 along at least one side of the channel 48 for at least one leg 32 of the tooth analog 24 are spaced apart from each other a certain, pre-defined distance that enables the technician moving the tooth analog 24 to quickly determine the extent of movement of the corresponding model crown 30. For instance, the tracks 46 may be constructed with a certain spacing between adjacent teeth 50 so that the technician can determine that the model crown 30 has been moved one-fourth millimeter in translation. In this example, the teeth 50 can provide tactile feedback in the nature of a "click" for each one-fourth millimeter movement of the model crown 30, so that the technician will readily know that the crown 30 has been moved one millimeter in translation after feeling four clicks.

With reference again to FIG. 1, the set of tooth analogs 24 optionally includes stationary tooth analogs such as a first lower left molar tooth analog 24b that is not intended to move during manufacture of a series of polymeric appliances. Consequently, the molar analog 24b need not be associated with a guide such as tracks 46. Instead, and in this example, the molar analog 24b includes a base 28b that comprises a single post 52b fixed to the upper level 42 of the platform 40. Optionally, the post 52b along with the corresponding model crown 30b are manufactured as a component integral with the platform 40. As a result, the position of the model crown 30b of the tooth analog 24b remains stationary during use of the apparatus 20.

The position of the stationary model crown 30b may represent the position of the corresponding lower left first molar of the patient before the beginning of treatment if movement of the patient's lower left first molar is not desired during the course of treatment. Alternatively, if the patient's tooth need only be moved a relatively small distance as can be accomplished in a single incremental step in order to reach its desired target position, the corresponding stationary tooth analog 24b may be constructed to support the model crown 30b in its intended target orientation. As a consequence, movement of the corresponding lower left first molar of the patient will begin as soon as the first polymeric appliance is worn even though the model crown 30b remains stationary during manufacture of the remaining series of polymeric appliances.

As yet another option, a relatively simple construction may be provided in instances where the only desired movement of the tooth analog 24 is movement in directions along the longitudinal axis of the model crown 30. As illustrated in the example of FIG. 1, a lower left second bicuspid tooth analog 24c includes a post 52b that is similar to post 52b, but instead is removably received in a matching socket that is either formed in the upper level 42 of the platform 40 or alternatively formed in the underside of the model crown 30c. In addition, a removable sleeve 54c is placed around the post 52c between the platform 40 and the model crown 30c, and the length of the sleeve 54c is selected by the technician to provide the desired height of the model crown 30c relative to the upper level 42 of the platform 40.

Preferably, a number of sleeves 54c of different lengths are available for the technician to use in instances where relatively large movements are desired. If the intended movement of the patient's corresponding tooth is in a downward direction (representing an intrusion movement of the tooth) the technician will select a series of sleeves 54c having progressively shorter lengths. After a polymeric appliance is made using the longest of the pre-selected sleeves 54c, that sleeve is removed and replaced with the next shorter sleeve of the series before manufacture of the next polymeric appliance. In this fashion, the model crown 30c will be supported in progressively lower positions relative to remaining model crowns during manufacture of the series of polymeric appliances.

In the embodiment depicted in FIG. 1, each of the tooth analogs 24 is either fixed to the platform 40 and retained in a stationary position during use of the apparatus 20 to make various appliances, or movably connected to the platform 40 so that its position may be changed during use of the apparatus 20 to make various appliances. However, the base 28 for many of the tooth analogs 24 has been omitted in FIG. 1 for purposes of illustration.

Use of the apparatus 20 in an exemplary system for making polymeric appliances will now be described. Initially, an orthodontic practitioner reviews the patient's malocclusion and determines an appropriate treatment plan that includes the desired final arrangement of the teeth at the conclusion of treatment. A digital data file representing the positions and shapes of the patient's teeth is obtained and used during construction of the apparatus 20 for making the model crowns 30. Optionally, the practitioner may also use the data file to review the malocclusion on a computer screen and determine the treatment plan.

If, for instance, an impression of the patient's teeth is taken at the practitioner's office, the impression may be scanned to create a digital data file representing the patient's malocclusion. Alternatively, a positive model (such as a model produced from plaster of Paris) may be made from the impression, and the model may be scanned to create the digital data file of the patient's malocclusion. As yet another alternative, an intra-oral scanner may be used to create a digital data file of the patient's malocclusion and thereby avoid the need for the practitioner to take an impression.

The data file of the patient's initial tooth arrangement is then modified in order to identify or create separate data files for each tooth crown. In one embodiment, the data file of the patient's initial dental arch is modified by using software that determines the boundaries of each tooth crown, so that independent movement of each tooth crown can be achieved. In another embodiment, a positive model of the patient's dental arch is sectioned by hand using a cutting tool after a scan of the maloccluded arch model has been made. The arch model is sectioned in such a manner that individual teeth are cut apart from adjacent teeth and scanned alone in order to create a separate digital data file for each tooth crown. These separate data files representing each crown surface can then be married to the earlier single scan that was taken of the maloccluded arch, with the result being individual, virtual tooth crowns that can be moved by software on a computer screen independently of adjacent tooth crowns.

Next, a transform function is determined that defines the path of travel of each tooth crown from its initial position to the desired, intended position as specified by the practitioner in a target tooth arrangement. In some instances, such as may be observed with some or all of the patient's molar teeth, little or no movement of the tooth may be desired as the patient progresses toward the conclusion of treatment. In other instances, one or more teeth may move through relatively large instances and/or along torturous paths in order to reach their intended target positions. Movements along the path of travel may include one or more translational movement of the tooth crown in x, y or z axis directions and/or one or more rotational movements $\alpha$, $\beta$, $\gamma$ of the tooth crown about each of the reference axes. These six degrees of freedom at any one point in time may be expressed collectively as a 3D Affine transform "T". Taken as a function of time over the period of treatment, the path that a tooth takes may be expressed as a transform function "T(t)". This function may be broken down into 6 separate functions that each describes a motion along or about a single axis: $x(t)$, $y(t)$, $z(t)$, $\alpha(t)$, $\beta(t)$, and $\gamma(t)$.

Subsequently, a set of data representing a tooth analog 24 is defined for each model tooth crown 30. In addition, a vector defining the longitudinal axis of each track 46 is determined for each of the tooth analogs 24, using a mathematical transformation to transform the corresponding vector defining the path of travel of the associated model crown 30. As mentioned earlier, the legs 32 of each tooth analog 24 can be oriented as necessary in order to avoid interference with the legs 32 of adjacent tooth analogs 24 during movement of the model crowns 30. Preferably, a computer is used with appropriate software to perform iterations as may be needed until a satisfactory orientation of each track 46 is determined for avoiding such interference.

The transform functions defining the longitudinal axes of the tracks 46 are then used to construct the platform 40 with appropriate channels 48. For example, a computer-controlled CNC milling machine may be used with appropriate cutters to precisely manufacture the channels 48 in a metallic sheet of material. Alternatively, the platform 40 (including various levels, if desired, and any interconnecting webs or framework) may be made and formed with appropriate channels 48 using a rapid prototyping process such as 3D printing, stereolithography or direct metal laser sintering.

The digital data files representing the tooth analogs 24 are used to construct the physical tooth analogs 24. Optionally, the tooth analogs 24 are made simultaneously with the manufacture of the platform 40 in a rapid prototyping process, such that the outer ends 38 of the legs 32 are formed in place in respective channels 48 using support material that is subsequently washed away after the legs 32 and channels 48 are formed. As a consequence, the need to manually assemble the tooth analogs 24 to the platform 40 can be avoided. As another alternative, the tooth analogs 24 are manufactured in an operation that is separate from manufacture of the platform 40, and the outer ends 38 have a shape only slightly larger than the width of the slots above the channels 48. In this latter alternative, the tooth analogs 24 and/or the tracks 46 are made of a material having sufficient resiliency that enables the outer ends 38 and/or tracks 46 to be slightly deformed and allow the outer ends 38 to be pushed through the slot openings above the channels 48 during assembly of the apparatus 20.

Preferably, the tracks 46 are constructed so that the first and second ends of the channels 48 are in contact with the legs 32 when the corresponding tooth analog 24 is in its initial and target or desired position, respectively. For example, when all of the outer ends 38 of the tooth analogs 24 are in contact with the first end of the channel 48 of the respective tracks 46, the model crowns 30 are in an orientation corresponding to the initial arrangement of the patient's teeth at the beginning of treatment. Likewise, when the outer ends 38 are in contact with the second end of the channels 48 of the respective tracks 46, the model crowns 30 of the tooth analogs 24 are in an arrangement corresponding to the desired target arrangement of the patient's teeth at the conclusion of treatment. In this manner, the technician can be assured that all of the model crowns 30 are in their initial positions or target positions by adjusting the tooth analogs 24 (by, e.g., pushing against the base 28) until such time as all of the outer ends 38 are in contact with the first or second ends of the corresponding channels 48 respectively.

However, as an additional or alternative confirmation, a full or partial impression of the patient's maloccluded teeth can be used to ensure that each of the model crowns 30 is initially oriented in a position precisely corresponding to the initial position of the respective tooth crown of the patient. For example, a partial impression taken of the patient's maloccluded teeth may be placed over the model crowns 30 and the tooth analogs 24 shifted along the tracks 46 as needed until such time as the impression can be fully seated over all of the model crowns 30. Preferably, the impression comprises a relatively hard material that does not unduly deform when in contact with the model crowns 30. As an alternative to using an impression, a negative model of the patient's maloccluded teeth may be may from the digital data file of the patient's maloccluded teeth using, for example, a rapid prototyping process.

As yet another option, the first ends of the channels 48 may be constructed to orient the tooth analogs 24 in an arrangement corresponding to the initial polymeric appliance to be manufactured instead of in an arrangement corresponding to the patient's initial malocclusion. Moreover, the second ends of the channels 48 may be constructed to orient the tooth analogs 24 in an arrangement that represents an overcorrection of the patient's teeth, such that the patient's teeth eventually drift toward a desired final arrangement some time after the final polymeric appliance of the series is worn.

Next, one or more of the tooth analogs 24 are incrementally moved as needed by the technician to intermediate tooth arrangements representing arrangements between initial and target arrangements of the patient's teeth. The tooth analogs 24 may be individually moved by pushing against the legs 32 or against other areas of the analogs 24 in order to slide the outer ends 38 an incremental step along the channels 48. After at least one of the tooth analogs 24 has been moved as desired to an intermediate position and the model crowns 30 are in a desired intermediate arrangement, a polymeric appliance is made. In FIG. 6, a sheet of polymeric material 60 has been placed over the model crowns 30 to make an appliance. Suitable polymeric materials for the sheet 60 include, for example, TRU-TAIN brand thermoplastic dental material, 0.03 thick, from Tru-Tain, Inc. of Rochester, Minn. The sheet of polymeric material 60 is softened using heat while subjected to pressure or vacuum until such time as the sheet has conformed to the shape and orientation of the model crowns 30 as repositioned.

Optionally, a quantity of material, designated 56 in FIG. 6 (and omitted in FIG. 1 for purposes of illustration), is received in the pan 22 and surrounds the base 28 including the legs 32 of each tooth analog 24. The quantity of material 56 can change from a first state that facilitates movement of the base 28 of each analog 24 relative to the platform 40 and to a second state that hinders movement of the base 28 relative to the platform 40. Consequently, the tooth analogs 24 can be moved manually by the technician without difficulty when the material 56 is in its first state and adjusted to precise positions as desired, and yet are securely held in a fixed position when the material 56 is in its second state in order to avoid inadvertent movement of the model crowns 30 during the time that the sheet of polymeric material 60 is formed over the model crowns 30.

The quantity of material 56 optionally comprises a composition having a viscosity that decreases as the temperature of the material 56 is increased. As one example, the quantity of material 56 may comprise a paraffin wax or a polyamide hot melt gelatin that softens upon exposure to heat. In addition, an electric heating element 58 is thermally connected to the pan 22 in order to increase the temperature of the material 56 when desired.

Optionally, a sufficient amount of the material 56 is present in the pan 22 such that the upper surface of the material 56 is just slightly above the lower peripheral edge of the model crowns 30. As a result, after the material 56 has been cooled to fix the tooth analogs 24 in place and the sheet of polymeric material 60 is placed over the model crowns 30 to make a polymeric appliance, the sheet 60 during softening does not deform in such a manner to extend into undercut regions beneath the bottom of each model crown 30. The resulting formed sheet of material 60 can then be removed from the model crowns 30 without undue difficulty.

Figure 7:
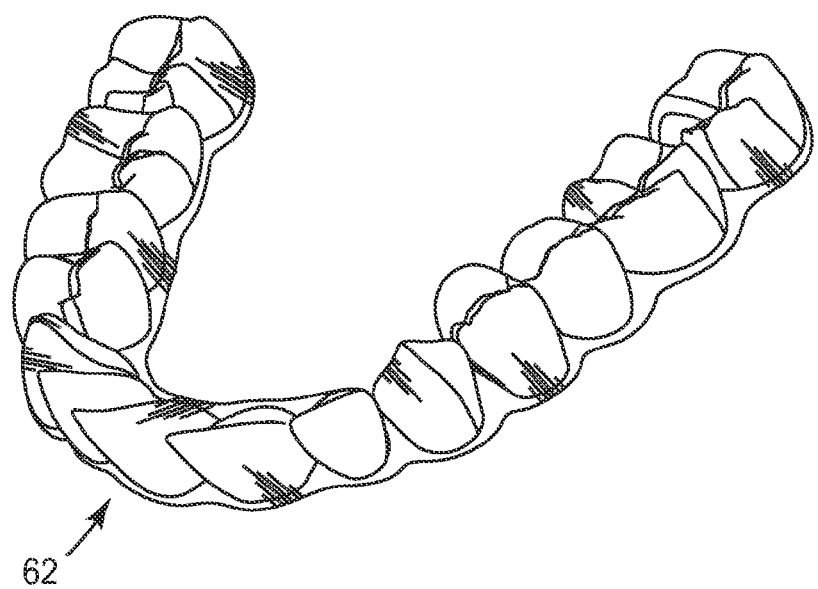
FIG. 7 is a reduced perspective view of a trimmed polymeric appliance that has been made using the apparatus illustrated in FIGS. 1 and 6.

The sheet 60 is trimmed as needed after it has been formed to the shape of the model crowns 30 in the chosen tooth arrangement in order to help insure that the resulting polymeric appliance is comfortable to wear. An exemplary polymeric appliance 62 is illustrated in FIG. 7. Optionally, a computer-controlled focused laser is used to trim the sheet of material 60 along a path that corresponds to the patient's gingival margin, or alternatively along a path that is closely adjacent the patient's gingival margin in either an occlusal or gingival direction.

Subsequently, the heating element 58 is energized in order to raise the temperature of the material 56 and lower its viscosity, enabling desired tooth analogs 24 to be moved as needed. The rows of ratchet teeth 50, if provided, help ensure that the legs 32 of the tooth analogs 24 are not inadvertently moved in a direction back toward their initial positions, but instead are moved, if at all, only in directions toward their intended target positions. The technician selects one or more of the tooth analogs 24 for movement in order to bring the associated model crowns 30 into desired a subsequent intermediate arrangement, and the steps recited above are repeated in order to manufacture the next polymeric appliance 62 to be worn in sequence by the patient. Further repetition of the steps mentioned above is carried out until all of the polymeric appliances 62 needed to move the patient's teeth to their intended target positions are manufactured.

The apparatus 20 provides significant advantages over conventional processes for fabricating polymeric appliances. One advantage is that a technician using the apparatus 20 can readily observe the various movements of the tooth analogs 24 from different viewpoints as may be desired and quickly form a mental understanding of possible interactions between neighboring model crowns 30. For example, the technician may observe that movement of one tooth analog 24 before an adjacent tooth analog 24 provides certain benefits such as avoidance of interference with adjacent model crowns in the same dental arch, a particular advantage when the patient's arch is relatively crowded. By enabling the technician to initially observe the various possibilities for sequence of movements and optionally conduct trial runs of potential sequences using the physical mock-up provided by the apparatus 20, it is possible to determine an optimal sequence of movements before any of the polymeric appliances 62 are made.

Another advantage of the apparatus 20 is that the cost of rapid prototyping materials can be significantly reduced in comparison to conventional processes that involve the fabrication of a positive model of the patient's dentition for each polymeric appliance. For example, the apparatus 20 can be used to make a complete sequence of polymeric appliances using only a sufficient amount of rapid prototyping material to form one set of the tooth analogs 24 and one platform 40. The apparatus 20 can also be reused during the course of treatment if the orthodontic practitioner determines that one or more additional intermediate appliances would be best for additional treatment. Similarly, if the patient relapses into malocclusion after the planned conclusion of treatment, the patient may reenter treatment, and the same tooth analogs 24 may be used along with the same or a different apparatus 20 to further correct the malocclusion. Moreover, the costs of purchasing and maintaining rapid prototyping machines as well as the time necessary for fabricating a series of positive rapid prototype models are also significantly reduced.

Figure 8:
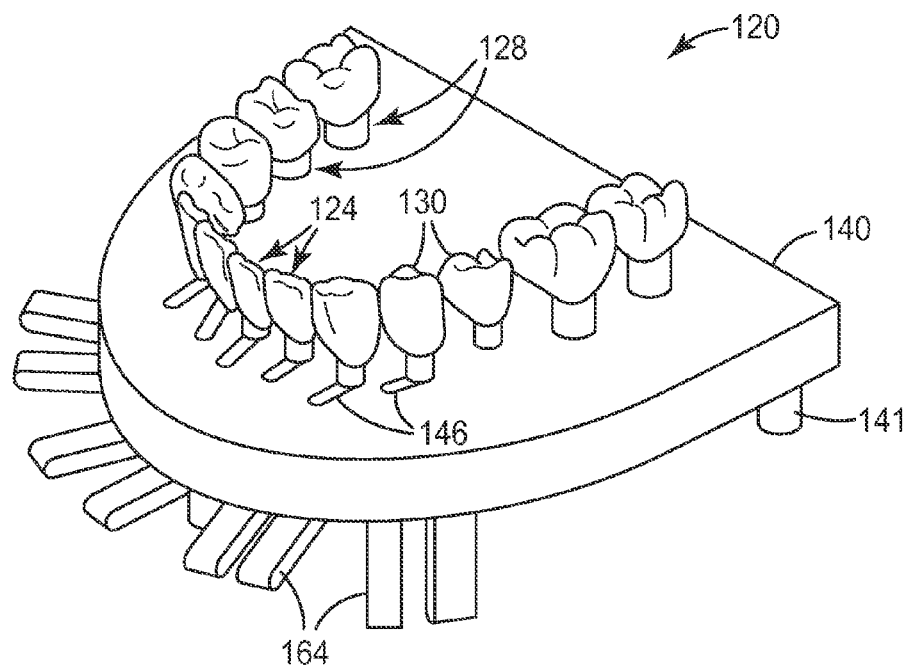
FIG. 8 is a perspective view of a portion of an apparatus for making a polymeric appliance according to another embodiment of the invention.
Figure 9:
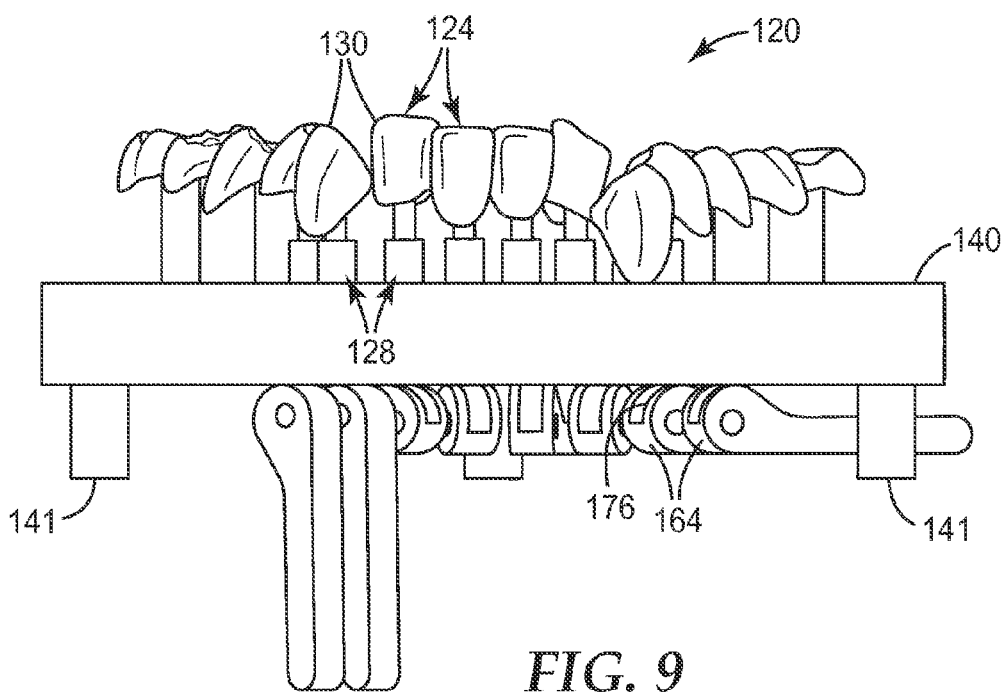
FIG. 9 is an enlarged rear view of the apparatus illustrated in FIG. 8.

An apparatus 120 according to another embodiment of the invention is illustrated in FIGS. 8 and 9. The apparatus 120 includes a series of tooth analogs 124, each of which includes a model crown 130 similar to the model crown 30 described above. Each of the tooth analogs 124 also includes a base 128 that is coupled to the respective model crown 130.

The apparatus 120 includes a platform 140 that includes a set of guides or tracks 146, each of which has a slot-like configuration. The base 128 of each tooth analog 124 that has been designated for movement extends through one of the tracks 146 and is coupled to a cam lever 164 that is located on a side of the platform 140 opposite the side adjacent the model crowns 130. In the illustrated embodiment, the cam levers 164 are located beneath the platform 140 and the platform 140 comprises a single level. The platform 140 also includes feet 141 that can be constructed with a length as desired to enhance access and/or clearance for the cam levers 164.

Figure 10:
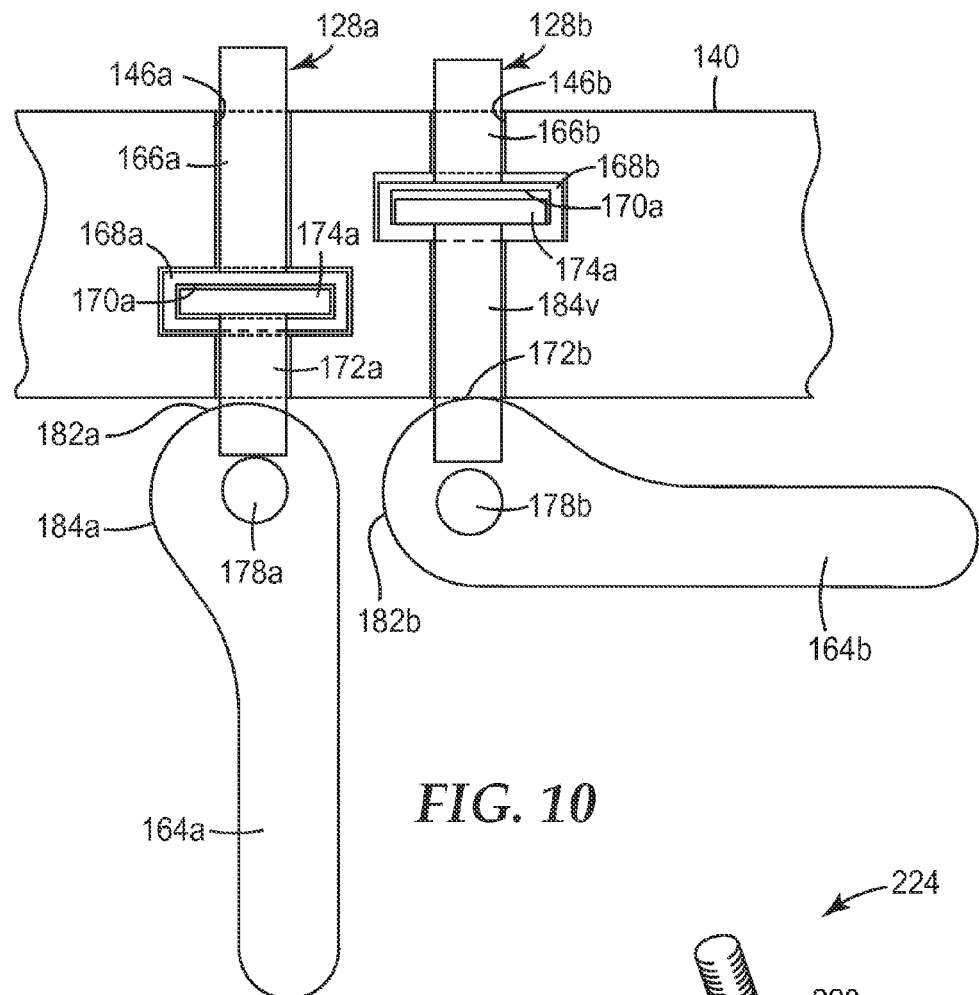
FIG. 10 is an enlarged side view in partial section of two cam levers and associated components of tooth analogs of the apparatus shown in FIGS. 8 and 9.

FIG. 10 depicts two exemplary tooth analog bases 128a, 128b and their corresponding cam levers 164a, 164b in more detail, looking in cross-section through a portion of the platform 140. The bases 128a, 128b in this example include an upper section 166a, 166b each with an enlarged, cylindrical lower end 168a, 168b having an internal cylindrical chamber 170a, 170b. The bases 128a, 128b also each include a lower section 172a, 172b having an enlarged, cylindrical upper end 174a, 174b that is received within the chamber 170a, 170b respectively. The bases 128a, 128b (including the lower ends 168a, 168b and adjacent regions of the upper and lower sections 168a, 168b, 172a, 172b) are each slidably received in an elongated guide or track 146a, 146b that extends along a pre-defined path within the platform 140. The tracks 146a, 146b include a channel with a cross-shaped configuration in a longitudinal cross-sectional view. The channel includes an intermediate cavity that receives the lower ends 168a, 168b. The channel of the tracks 146a, 146b also includes upper and lower cavities that are somewhat smaller than its intermediate cavity and receive the upper and lower sections 166a, 166b, 172a, 172b respectively.

A lower portion of the lower sections 172a, 172b extends through a slot 176 (see FIG. 9) in the levers 164a, 164b and includes a cylindrical cross-bar 178a, 178b. The cross-bars 178a, 178b are pivotally received in aligned, cylindrical bores of a bifurcated upper end of each cam lever 164a, 164b. The cam levers 164a, 164b have a smooth, outer curved surface with a varying radius of curvature relative to the center of the bores, ranging from a first portion 182a, 182b having a relatively larger radius of curvature to a second portion 184a, 184b having a relatively smaller radius of curvature.

The cam lever 164a shown in the example of FIG. 10 is in an orientation that permits free sliding movement of the base 128a relative to the platform 140. To this end, the curved surface portion 182a is constructed with a sufficiently small radius to avoid contact, or at least firm contact, with the underside of the platform 140. In this position of the cam lever 164a, the upper end 174a of the lower section 172a is freely movable relative to the lower end 168a of the upper section 166a, and lower end 168s is freely movable relative to the walls defining the intermediate cavity of the channel of the track 146a. As a result, the technician is able to move the base 128a along the track 146a with relatively little effort.

The cam lever 164b in the example of FIG. 10 has been moved from a vertical orientation similar to the illustrated example of the cam lever 164a to a horizontal orientation as shown in the drawing in order to releasably retain the base 128b along with its associated model crown 130 in a desired position. During such movement of the cam lever 164b, the cam lever 164b pivots about the central axis of the crossbar 178b and causes the larger curved surface portion 182b to come into contact with the underside of the platform 140 and move the lower section 172b in a downward direction. This downward movement of the lower section 172b continues as the cam lever 164b pivots until the upper end 174b pulls the lower end 168b into a position of firm engagement with the bottom of the intermediate cavity of the track 146b. In this orientation of the cam lever 164b, both the lower section 172b and the upper section 166b are releasably locked into fixed positions relative to each other as well as relative to the platform 140.

In the illustrated embodiment, the upper and lower sections 168a, 168b, 172a, 172b have circular cross-section when viewed in a horizontal reference axis. As a result, the technician can pivot the associated model crowns 130 in directions about their long axes as desired when the cam levers 164 are in the orientation shown for the cam lever 164a. In addition, the cam levers 164a, 164b can be pivoted about the longitudinal axes of their corresponding upper sections 172a, 172b as may be desired to enhance accessibility and/or avoid interference with adjacent cam levers 164. If desired, the underside of the platform 140 may have a stepped configuration, wherein adjacent cam levers 164 are arranged into two or more levels to further enhance accessibility and/or avoid interference with adjacent cam levers 164.

As another alternative, the upper sections 166a, 166b may have a non-circular cross-section, such as an oval-shaped cross-section or a rectangular cross-section. In this alternative construction of the apparatus 120, the upper cavity of the track 146a, 146b has a width that is sufficiently narrow to prevent significant relative rotation of the upper sections 166a, 166b about their longitudinal axes relative to a reference tangent line extending from a point on the directly adjacent portion of the path of the track 146. As a consequence, the rotational orientation of the corresponding model crown 130 relative to the platform 140 is determined by the orientation of the vertical walls defining the upper cavity as the base 128 of the tooth analog 124 moves along the track 146.

The tracks 146 are constructed to guide and enable movement of the corresponding bases 128 in directions that cause the model tooth crowns 130 to move along pre-determined, intended paths of travel. Similar to the tracks 46, the tracks 146 can extend along curved or straight paths, and/or extend along inclined paths that rise or fall in a vertical direction so long as the thickness of the portion of the platform 140 adjacent the tracks 146 does not change. The width of the cam levers 164 can also be reduced from that shown in the drawings to avoid contact with adjacent cam levers 164.

The apparatus 120 is placed in a vacuum or pressure molding machine for making a series of polymeric appliances in a manner somewhat similar to the method described above for making polymeric appliances 62 using the apparatus 20. An example of a suitable molding machine is the "BIOSTAR" brand pressure molding machine with an infrared heater from Scheu-Dental of Iserlohn, Germany. Preferably, a quantity of stainless steel pellets is placed in the molding machine in a sufficient amount to cover the undercuts beneath the model crowns 130 so that a thermoplastic sheet when softened to form a appliance does not reach into the undercut areas and subsequently hinder removal of the formed sheet from the model crowns 130.

Other aspects and options described above in connection with the apparatus 20 may be used in connection with the apparatus 120. For example, the apparatus 120 may include one or more stationary tooth analogs similar to analog 24b shown in FIG. 1. The apparatus 120 may also include on or more tooth analogs that can be moved in incremental steps in a vertical direction similar to the analog 24c.

Figure 11:
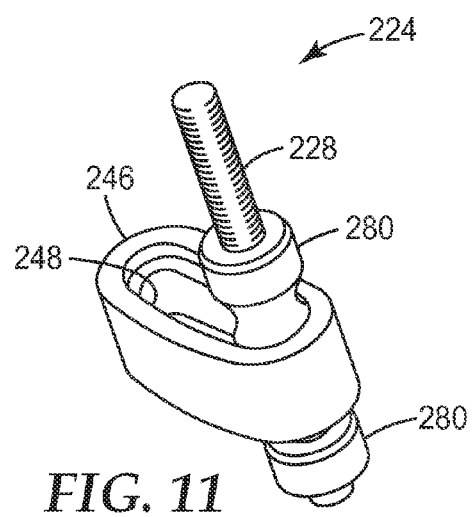
FIG. 11 is an enlarged perspective view of a portion of an alternative tooth analog that can optionally be used with the apparatus shown in FIGS. 1 and 6 or with the apparatus shown in FIGS. 8 and 9.

FIG. 11 is an enlarged illustration of a portion of a tooth analog 224 that may be used as a replacement or alternative to the tooth analogs 24, 124 described above. The tooth analog 224 includes a model crown (not shown) that is threaded onto a top portion of an elongated, threaded base 228. The base 228 extends through an elongated channel 248 of a guide or track 246 having a slot-like configuration. Two nuts 280 optionally in the form of knurled thumbscrews are threaded onto the base 228 and are located on opposite sides of the track 246. Optionally, the elongated channel 248 may include one or more steps parallel to the main path of travel that permit a portion of the nut(s) 280 to recess into the surface(s) of track 246. Such a stepped configuration may provide additional embrasure of the base/nuts assembly and thus more positive guidance along the track.

The track 246 is part of a platform that is not shown in FIG. 11. However, the platform could have a solid cross-section between adjacent tracks such as shown in the FIGS. 8-10 with respect to the platform 140. As another alternative, the platform interconnecting the tracks 246 could have a web-like cross-section, with finger-like extensions connecting adjacent tracks 246 to each other in order to reduce the expense of the platform material. Such a construction is especially advantageous in instances where the platform is made using a rapid-prototyping process.

The track 246, similar to the tracks 46, 146, may rise and/or fall along its length, and/or extend along a straight or curved path in accordance with the desired path of travel of the associated model crown. When the technician determines that the model crown associated with the base 228 is in a desired position for forming a polymeric appliance, the nuts 280 are tightened against the track 246 to releasably lock the tooth analog 224 in place. The height of the attached model crown may be adjusted by first loosening the nuts 280 and then turning them by equal amounts in the same direction, thus changing the position of the base 228 relative to the track 246. As an option, the base 228 may have a non-circular cross-section (as described above in connection with the upper section 166 of the base 128) in order to maintain the attached model crown in a certain, pre-determined rotational orientation relative to the channel 248.

Figure 12:
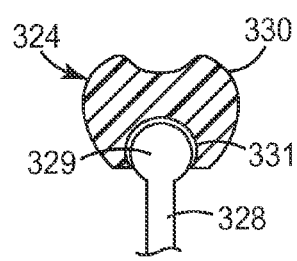
FIG. 12 is an enlarged side cross-sectional view of a portion of a tooth analog according to another embodiment of the invention.

FIG. 12 illustrates an upper portion of a tooth analog 324 according to another embodiment of the invention. The tooth analog 324 includes a model crown 330 that has a configuration similar or identical to the crown of one of the patient's teeth. The tooth analog 324 also includes a base 328 that is connected to the model crown 330 by an adjustable joint. The joint includes a ball 329 that is fixed to the upper end of the base 328 and a socket 331 that is formed in a lower portion of the model crown 330.

Preferably, the ball 329 closely fits into the socket 331 so that the model crown 330 is held in place by friction during forming of a polymeric appliance. As such, the technician can adjust the orientation of the model crown 330 to any one of a number of different positions before the appliance is formed. The ball-and-socket joint enable the model crown 330 to be moved in additional degrees of rotation relative to the base 328 (depending upon the path of the track), a distinct advantage in instances when the tracks guiding the movement of the tooth analog 324 (such as tracks 46, 146, 246) extend in directions along a flat reference plane. However, the embodiment shown in FIG. 12 can be used with any of the embodiments described earlier.

A variety of other options are also possible. As one example, instead of tracks presenting a hollow channel, the tracks could have a solid cross-section in the nature of continuous elongated rails that extend through corresponding holes in the base of the tooth analog, wherein the rails are constructed to extend along paths of travel sufficient to guide the associated model crown along its desired path. Optionally, the rails could be threaded and provided with nuts (similar to nuts 80) to releasably lock the associated tooth analog in a fixed position for making a polymeric appliance.

As another example, it may be desirable in certain treatments to provide two or more apparatus somewhat similar to the apparatus 20, 120 so that the method of making a series of polymeric appliances can be segmented into two or more stages. The latter example is particularly useful in instances where it would otherwise be difficult to construct guides or move tooth analogs along certain complete paths between initial and target positions due to interference with other guides or tooth analogs. Other options include combining the various tooth analogs and/or platforms described above. In addition, instead of forming each polymeric appliance in sequence to match the intended sequence of use by the patient, it is possible to construct the series of polymeric appliances in a reverse sequence; i.e. by initially forming a polymeric appliance when all of the model crowns are in their desired target positions and then moving one or more of the model crowns toward their initial, maloccluded positions.

Those skilled in the art may recognize that other options are also possible without departing from the spirit of the invention. Consequently, the invention should not be deemed limited to the embodiments described above in detail, but only by a fair scope of the claims that follow.

The invention claimed is:

1. A method of making a polymeric orthodontic appliance comprising:
   providing a set of physical tooth analogs each having a model tooth crown with a shape that is representative of the shape of a respective tooth crown in a patient's dental arch, the crown having labial and lingual exterior surfaces, and wherein the physical tooth analogs are arranged in an arch;
   obtaining data for at least some of the tooth analogs that represents a path of movement for the corresponding model crown to a desired position;
   using the data to construct a set of guides for guiding the movement of the tooth analogs in such a manner that the respective model crowns are moved along corresponding paths, wherein at least some of the guides comprise channels in a platform having a longitudinal axis and first and second closed ends, the axis arranged in directions that define at least a portion of the path of movement for the corresponding model crown, and wherein at least one of the channels extends to the second closed end in a direction away from the arch to define an arch exterior channel, the second end displaced in a labial direction from the labial surfaces of the corresponding model crown and the arch when the arch exterior channel extends at least partially in a labial direction and displaced in a lingual direction from the lingual surfaces of the corresponding model crown and the arch when the arch exterior channel extends at least partially in a lingual direction;
   moving one or more of the tooth analogs along their respective channels as needed in order to bring the corresponding model crown an incremental step either toward or away from its desired position; and
   forming the polymeric appliance over the model crowns after at least one of the tooth analogs has been moved.

2. The method of claim 1 wherein at least one guide includes a track, and wherein at least one tooth analog includes at least one leg that is received in the track.

3. The method of claim 2, wherein the physical tooth analogs are arranged in an arch, wherein at least one guide includes at least three tracks, wherein at least one tooth analog includes at least three legs each having an outer end that is received in a respective track, and wherein one track is located outside the arch.

4. The method of claim 1 wherein each guide includes structure that hinders movement of the tooth analog in one direction along the guide.

5. The method of claim 4 wherein the structure comprises ratchet structure, the ratchet structure hindering movement within the channels.

6. The method of claim 5 wherein the ratchet structure includes a row of inclined ratchet teeth in contact with the tooth analog, and wherein the ratchet teeth are deformable to facilitate movement of the tooth analog in one direction and hinder movement of the tooth analog in an opposite direction.

7. The method of claim 6, wherein the tooth analog comprises a base with a leg in contact with the channel, and wherein the row of ratchet teeth is connected to the channel and in contact with the leg.

8. The method of claim 1 wherein each tooth analog includes a base that is received in a pan containing a quantity of material, and wherein the quantity of material can change from a first state that facilitates movement of the base relative to the pan and to a second state that hinders movement of the base relative to the pan.

9. The method of claim 8 and including a heating element thermally connected to the pan, and including the act of activating the heating element in order to decrease the viscosity of the quantity of material.

10. The method of claim 1 wherein each channel comprises a first end and a second end opposite the first end, and wherein the model crown is in a position corresponding to the initial position of the patient's tooth when the tooth analog is located adjacent the first end of the channel.

11. The method of claim 1 wherein the model crown is in a position corresponding to the desired target position of the patient's tooth when the tooth analog is located adjacent the second end.

12. The method of claim 1 wherein at least one guide comprises an elongated slot, and wherein the tooth analog includes a base that extends through the slot.

13. The method of claim 12 wherein the base includes threads and wherein the tooth analog further includes a nut received on the threads for selectively securing the tooth analog in a fixed position relative to the guide.

14. The method of claim 13 wherein the base is elongated and is movable in directions along its longitudinal axis in order to change the height of the model crown.

15. The method of claim 12 wherein the tooth analog includes a cam lever pivotally connected to the base, and wherein the cam lever is operable to selectively secure the base in a fixed position relative to the guide.

16. The method of claim 1, wherein at least one of the channels extends between the first and second closed ends along an inclined path in a vertical direction.

17. The method of claim 16, and including a sleeve removably coupled to one of the bases, and wherein the method further includes the act of selecting the length of the sleeve for positioning the corresponding model crown at a desired height.

18. The method of claim 1 wherein at least one tooth analog remains in a stationary position as at least one of the remaining tooth analogs is moved.

19. The method of claim 1 and including the act of making the guides using a rapid prototyping process.

20. The method of claim 1 and including the acts of subsequently moving at least one tooth analog along its respective guide as needed in order to bring the model crowns into a subsequent crown arrangement and subsequently forming a second polymeric appliance over the model crowns.

21. The method of claim 1 wherein the act of moving one or more of the tooth analogs along its respective guide is carried out by pushing the one or more tooth analogs by hand.

\* \* \* \* \*